(12) United States Patent
Lee et al.

(10) Patent No.: US 10,130,168 B2
(45) Date of Patent: Nov. 20, 2018

(54) MULTI-FUNCTIONAL TABLE AND TABLE CONTROL SYSTEM

(71) Applicant: GAZELAB Inc., Seoul (KR)

(72) Inventors: Gap Hyun Lee, Seoul (KR); Ju Youn Lee, Seoul (KR)

(73) Assignee: GAZELAB Inc., Seoul (KR)

( * ) Notice: Subject to any disclaimer, the term of this patent is extended or adjusted under 35 U.S.C. 154(b) by 0 days.

(21) Appl. No.: 15/371,997

(22) Filed: Dec. 7, 2016

(65) Prior Publication Data

US 2017/0354244 A1 Dec. 14, 2017

(30) Foreign Application Priority Data

Jun. 14, 2016 (KR) .......................... 10-2016-0073877

(51) Int. Cl.
| | |
|---|---|
| *A47B 21/02* | (2006.01) |
| *A47B 9/20* | (2006.01) |
| *A47B 37/00* | (2006.01) |
| *A61B 5/11* | (2006.01) |
| *A61B 5/103* | (2006.01) |
| *H04M 1/725* | (2006.01) |
| *G08B 21/04* | (2006.01) |
| *G08B 5/36* | (2006.01) |

(52) U.S. Cl.
CPC ................ *A47B 21/02* (2013.01); *A47B 9/20* (2013.01); *A47B 37/00* (2013.01); *A61B 5/1036* (2013.01); *A61B 5/1116* (2013.01); *A47B 2200/008* (2013.01); *A47B 2200/0052* (2013.01); *A47B 2200/0056* (2013.01); *A47B 2200/0061* (2013.01); *A47B 2200/0062* (2013.01); *A47B 2200/0098* (2013.01); *G08B 5/36* (2013.01); *G08B 21/0446* (2013.01); *H04M 1/72527* (2013.01)

(58) Field of Classification Search
CPC ............ A47B 21/02; A47B 2200/0052; A47B 2200/0056; A47B 2200/0061; A47B 2200/0062; A47B 2200/008; A47B 2200/0098; A47B 37/00; A47B 9/20; H04M 1/72527; A61B 5/1036; A61B 5/1116; G08B 21/0446; G08B 5/36; H01M 1/72527
See application file for complete search history.

(56) References Cited

U.S. PATENT DOCUMENTS

| | | | | |
|---|---|---|---|---|
| 5,323,695 | A * | 6/1994 | Borgman ................. | A47B 9/00 108/147 |
| 6,580,360 | B1 * | 6/2003 | McKee .................. | G06Q 10/06 340/286.09 |
| 6,964,370 | B1 * | 11/2005 | Hagale ................. | A47C 31/008 235/380 |
| 9,486,070 | B2 * | 11/2016 | Labrosse ................ | A47B 21/02 |

(Continued)

*Primary Examiner* — Kidest Bahta
(74) *Attorney, Agent, or Firm* — Novick, Kim & Lee, PLLC; Sang Ho Lee (57) ABSTRACT

A multi-functional table is provided. The multi-functional table includes at least one plate, at least one support part connected to the at least one plate and adjusting a height of each of the at least one plate, a communication part receiving user information from a user terminal, and a controller part controlling operations of the at least one support part in response to the user information which is received from the communication part.

19 Claims, 8 Drawing Sheets

(56) References Cited

U.S. PATENT DOCUMENTS

| | | | | |
|---|---|---|---|---|
| 2002/0167486 A1* | 11/2002 | Tan | ............... | B60N 2/002 345/156 |
| 2003/0025601 A1* | 2/2003 | Gruteser | ............ | A47C 15/004 340/540 |
| 2008/0245279 A1* | 10/2008 | Pan | ............... | A47B 9/00 108/144.11 |
| 2016/0260019 A1* | 9/2016 | Riquelme Ruiz | .... | A47B 21/007 |

* cited by examiner

MULTI-FUNCTIONAL TABLE AND TABLE CONTROL SYSTEM

CROSS-REFERENCE TO RELATED APPLICATION

This application claims priority to Korean Patent Application No. 10-2016-0073877, filed on Jun. 14, 2016, the disclosure of which is incorporated herein by reference in its entirety.

BACKGROUND

The present disclosure relates to a multi-functional table and a table control system, and more particularly, to a multi-functional table and a table control system wherein a height of the multi-functional table is automatically adjusted in accordance with user information such as user's physical conditions and so on.

Generally, a desk or table (hereinafter, referred to as "table") is an item of furniture that is used for reading, writing, eating, using a computer, various kinds of working, and so on. The table includes one or more supports and a plate spaced apart from the floor by a predetermined height by the supports.

In conventional practices, tables are designed and made according to the standard height obtained with a user's average physical conditions such as his or her average height or sitting height. Also, tables capable of adjusting height in accordance with a user's various physical characteristics or working environments have been widely released on the market recently so that the heights of the tables are optimized for the users.

On the other hand, in recent times, health problems for people who study or work for long hours while sitting at a table have been issued as a social problem, and especially, if they work for very long hours in a sitting position, their spinal health may have a problem. Accordingly, there is a growing interest in improving spinal health through proper postures. Therefore, there are definite needs for the development of a table capable of solving the health problems caused by improper postures and improving a user's conveniences and working efficiencies.

SUMMARY OF THE DISCLOSURE

Accordingly, in view of the above-mentioned problems occurring in the prior art, the present disclosure has been made and it is an object of the present disclosure to provide a multi-functional table and a table control system wherein the height of the multi-functional table is automatically adjusted in accordance with user information such as a user's physical conditions and so on.

To accomplish the above-mentioned object, according to a first aspect of the present disclosure, a multi-functional table includes at least one plate, at least one support part connected to the at least one plate and adjusting a height of each of the at least one plate, a communication part receiving user information from a user terminal, and a controller part controlling operations of the at least one support part in response to the user information which is received from the communication part.

The at least one plate includes a first plate and a second plate, and the first plate and the second plate are arranged not to overlap one another.

The user information includes operation mode information having at least one of a sitting mode and a standing mode.

The controller part has a configuration to control the at least one support part to adjust the height of each of the at least one plate according to the operation mode.

The user information further includes holding time information for each of at least one of the sitting mode and the standing mode, and if the holding time of the sitting mode has elapsed during the sitting mode, the controller part controls the at least one support part to adjust the height of each of the at least one plate as set in the standing mode, and if the holding time of the standing mode has elapsed during the standing mode, the controller part controls the at least one support part to adjust the height of each of the at least one plate as set in the sitting mode.

The controller part transmits alarming information to the user terminal if the holding time of at least one of the sitting mode and the standing mode has elapsed.

The user information includes at least one of user identification information and user physical information. The user identification information includes at least one of user identification and a user name, and the user physical information includes at least one of the following: sex, age, height, weight, and sitting height.

The controller part controls the at least one support to adjust the height of each of the at least one plate in response to at least one of the user identification information and the user physical information.

The multi-functional table can further include an approach sensing part sensing an approach of the user terminal to produce approach information, and a lamp disposed on the at least one of the plate. If the controller part receives the approach information from the approach sensing part, the lamp is turned on by the control of the controller part.

The multi-functional table can further include an input part receiving selection information for the sitting mode or the standing mode from the user.

When no selection information is received and the multi-functional table is in a standby mode, each of the at least one plate has a same height.

The controller part has a configuration to repeatedly change the modes between the sitting mode and the standing mode for a predetermined times.

The controller part has a configuration to change the modes between the sitting mode and the standing mode based on holding time of at least one of the sitting mode and the standing mode. The at least one plate includes more than two plates.

According to another embodiment of the present disclosure, a table control system is provided. The table control system includes a user terminal producing user information, and a multi-functional table having at least one plate, at least one support part connected to the at least one plate and adjusting a height of each of the at least one plate, a communication part receiving user information from a user terminal, and a controller part controlling operations of the at least one support part in response to the user information which is received from the communication part. Here, the multi-functional table adjusts the height of each of the at least one plate in response to the user information transmitted from the user terminal.

The user information comprises operation mode information having at least one of a sitting mode and a standing mode.

The table control system can include a posture sensing part sensing a user posture through pressures and positions of the user's feet. If the user's posture is sensed as deviated a predetermined posture in the standing mode, the posture sensing part transmits alarming information to at least one of the user terminal and a lamp disposed on the at least one plate.

The table control system further includes a seating part sensing a sitting time of the user and transmitting the sitting time to the controller part. If the sitting time exceeds a predetermined period of time in the sitting mode, the controller transmits alarming information to at least one of the user terminal and a lamp disposed on the at least one plate.

BRIEF DESCRIPTION OF THE DRAWINGS

The above and other objects, features and advantages of the present disclosure will be apparent from the following detailed descriptions of the embodiments of the disclosure in conjunction with the accompanying drawings, in which.

DETAILED DESCRIPTION OF THE PREFERRED EMBODIMENT

Hereinafter, the present disclosure is disclosed with reference to the attached drawings wherein the corresponding parts in the embodiments of the present disclosure are indicated by corresponding reference numerals and the repeated explanation on the corresponding parts will be omitted. If it is determined that the detailed explanations on a known technology related to the present disclosure makes the scope of the present disclosure unclear, the explanation will be omitted for the brevity of the description.

When it is said that one element is described as being "connected" or "coupled" to the other element, one element may be directly connected or coupled to the other element, at the same time, it may also be understood that another element may be present between the two elements.

"Based on" does not mean "based only on", unless expressly specified otherwise. In other words, the phrase "based on" describes both "based only on," "based at least on," and "based at least in part on." In the claims, as well as in the specification, all transitional phrases such as "comprising," "including," "carrying," "having," "containing," "involving," "holding," "composed of," and the like are to be understood to be open-ended, i.e., to mean including but not limited to.

Terms, such as the first, the second, A, B, (a) and (b) may be used to describe various elements, but the elements should not be restricted by the terms. The terms are used to only distinguish one element from the other element. For example, a first element may be named a second element without departing from the scope of the present disclosure.

Figure 1:
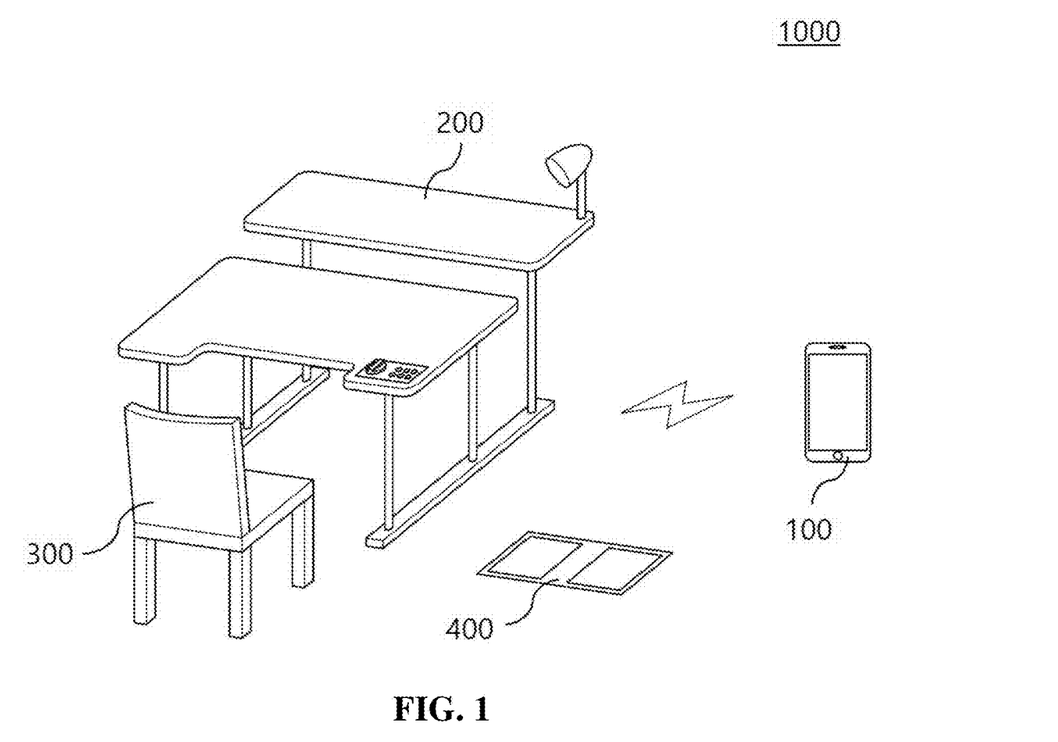
FIG. 1 is a perspective view showing a table control system according to one embodiment of the present disclosure.

FIG. 1 is a perspective view showing a table control system according to the embodiment of the present disclosure.

Referring to FIG. 1, a table control system 1000 includes a user terminal 100, a multi-functional table 200, a seating part 300, and a position sensing part 400.

The user terminal 100 may produce user information so as to adjust a height of the multi-functional table 200. For example, the user terminal 100 may produces the user information at a user's control via a computer application installed on the user terminal 100 so as to adjust the height of the multi-functional table 200. Through the computer application, the selection of operation modes of the multi-functional table 200 and the adjustment of height of the multi-functional table 200 can be carried out.

The user information includes operation mode information having at least one of a sitting mode and a standing mode; holding time information for at least one of the sitting mode and the standing mode; user identification information having a user identification, a user name and so on; and a user physical information having the user's sex, age, height, weight, sitting height and so on. In this case, the sitting mode refers to a mode in which the height of the multi-functional table 200 is appropriately set and is adequate for the user who is in a sitting position. The standing mode refers to a mode in which the height of the multi-functional table 200 is appropriately set for the user who is in a standing position.

The user terminal 100 may transmit the user information to the multi-functional table 200 through the user's manipulation. The user terminal 100 may transmit the user information to the multi-functional table 200, while the user terminal 100 is paired with the multi-functional table 200 through a wireless communication module (not shown). However, the example is not limited thereto.

If the holding time for the sitting mode and/or the standing mode set by the user has elapsed, the user terminal 100 displays the elapsed time on a display screen. Accordingly, the user can check the display screen and change his or her posture, for example, from the sitting position to the standing position or from the standing position to the sitting position. Further, the user terminal 100 can display alarming information transmitted from the multi-functional table 200 on the display screen. For example, the alarming information may include information that the holding time of the sitting mode and/or the standing mode set by the user has elapsed, the information that the user's posture deviates a predetermined range, and the information that the sitting time of the user in the sitting mode exceeds a predetermined period of time.

The user information 100 includes a smart phone having a wireless communication function, a personal digital assistant PDA having a wireless communication function, a portable computer having a wireless communication function, a photographing device like a digital camera having a wireless communication function, a gaming device having a wireless communication function, a music storing and reproducing household appliance having a wireless communication function, an internet household appliance capable of wireless internet accessing and browsing, and a portable unit or terminal in which the above-mentioned functions are combined, but is not limited thereto.

The multi-functional table 200 receives the user information and/or the selection information for the operation mode inputted by the user from the user terminal 100 and adjusts the height of at least one plate independently in response to the received information. In more detail, the multi-functional table 200 adjusts each height of a plurality of plates independently according to at least one of the holding time information, the user identification information, the user physical information, which are included in the user information, and the information of the operation mode, which can include the sitting mode and the standing mode.

If the operation mode of the user information is in the sitting mode, for example, the multi-functional table 200 can adjust the height of at least one of the plurality of plates so that it has a predetermined height in response to the sitting mode. Further, for example, if the user identification information and/or the user's physical information are further included in the user information, the multi-functional table 200 additionally adjusts the height of at least one of the plurality of plates so that it has a predetermined height set in response to the user identification information and/or a predetermined height set in response to the user's physical information.

On the other hand, if the holding time for the sitting mode, which is stored in the user information and set for the operation mode, has elapsed, the multi-functional table 200 is configured to automatically adjust the height of at least one plate from a height for the sitting mode to a height for the standing mode. According to another exemplary of the embodiment of the present disclosure, in such a situation, the multi-functional table 200 is configured to adjust the height of at least one plate in response to an input command from the user, such as a command of the standing mode, which converts the mode to the standing mode. Accordingly, the multi-functional table 200 guides the user to change his or her posture and helps the user not to use the multi-functional table 200 more than a predetermined time in one mode, i.e. sitting mode. Accordingly, the multi-functional table 200 improves the user's spinal health via the change of the user's posture.

Likewise, if the holding time for the standing mode, which is stored in the user information and set for the operation mode, has elapsed, the multi-functional table 200 is configured to automatically adjust the height of at least one plate from a height for the standing mode to a height for the sitting mode. According to another exemplary of the embodiment of the present disclosure, in such a situation, the multi-functional table 200 is configured to adjust the height of at least one plate in response to an input command from the user, such as a command of the sitting mode, which converts the mode to the sitting mode. Accordingly, the multi-functional table 200 guides the user to change his or her posture and helps the user not to use the multi-functional table 200 more than a predetermined time in one mode, i.e. standing mode. Accordingly, the multi-functional table 200 improves the user's spinal health via the change of the user's posture.

On the other hand, the transmission of the user information from the user terminal 100 to the multi-functional table 200 is carried out when the user terminal 100 is located within a predetermined range from the multi-functional table 200.

The seating part 300 is configured to sense a sitting time of the user and to transmit the sitting time to the multi-functional table 200. For example, the seating part 300 may be a chair or a part of a chair of the multi-functional table 200. If the sitting time exceeds a predetermined period of time, the multi-functional table 200 transmits alarming information to the user terminal 100, thereby alarming the user using the multi-functional table 200 more than the predetermined period of time in one mode. Accordingly, a portion of the seating part 300, which is for example an area in which the user sits, is provided with a sensor i.e. a pressure sensor or a proximity sensor to sense whether the user sits or not and to sense the sitting time.

The posture sensing part 400 can be configured to be in a mat-form which can sense the user's posture based on the pressures and positions of the user's both feet in the standing mode. The posture sensing part 400 transmits information about the user's posture to the user terminal 100. The posture sensing part 400 is configured to transmit alarming information to the user terminal 100, if it is determined that the user's posture deviates a predetermined range, in which, for example, the pressure of one side foot or a portion of the foot is greater than a reference value, or one side foot is located distant farther than a reference distance from a center of the posture sensing part 400. Accordingly, the user can correct his or her posture and have a correct posture.

On the other hand, the table control system 1000 further includes a physical body measuring part (not shown in FIG. 1). The physical body measuring part produces the physical information like the user's height, weight, and sitting height; and transmits the physical information to the user terminal 100 and/or the multi-functional table 200. In accordance with the physical information, the user terminal 100 and/or the multi-functional table 200 automatically set the heights of the plurality of plates in the sitting mode and/or the standing mode. According to the embodiment of the present disclosure, the physical body measuring part may include a variety of measuring sensors. For example, the physical body measuring part includes a height measuring sensor using ultrasound. According to the embodiment of the present disclosure, further, the user terminal with a predetermined application capable of measuring a body height functions as the physical body measuring part and directly uses the measured physical information. Otherwise, the measured physical information is transmitted to the multi-functional table 200.

Hereinafter, the details of the structure and operation of the multi-functional table 200 will be described further with reference to FIGS. 2 to 6.

Figure 2:
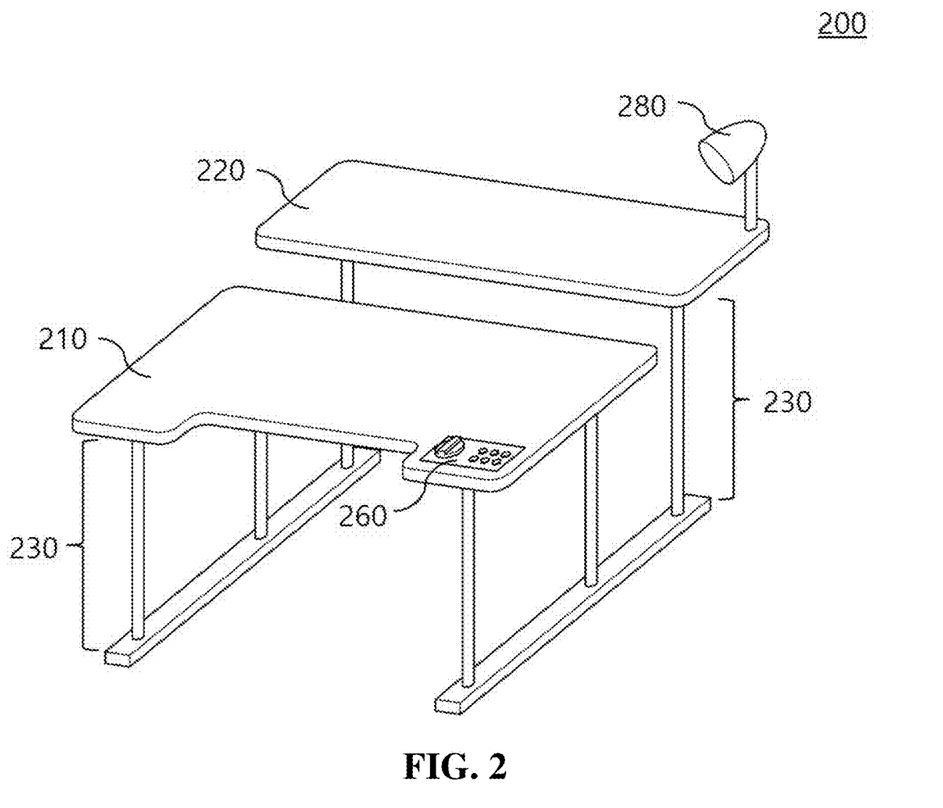
FIG. 2 is a perspective view showing a structure of a multi-functional table according to the embodiment of the present disclosure.
Figure 3:
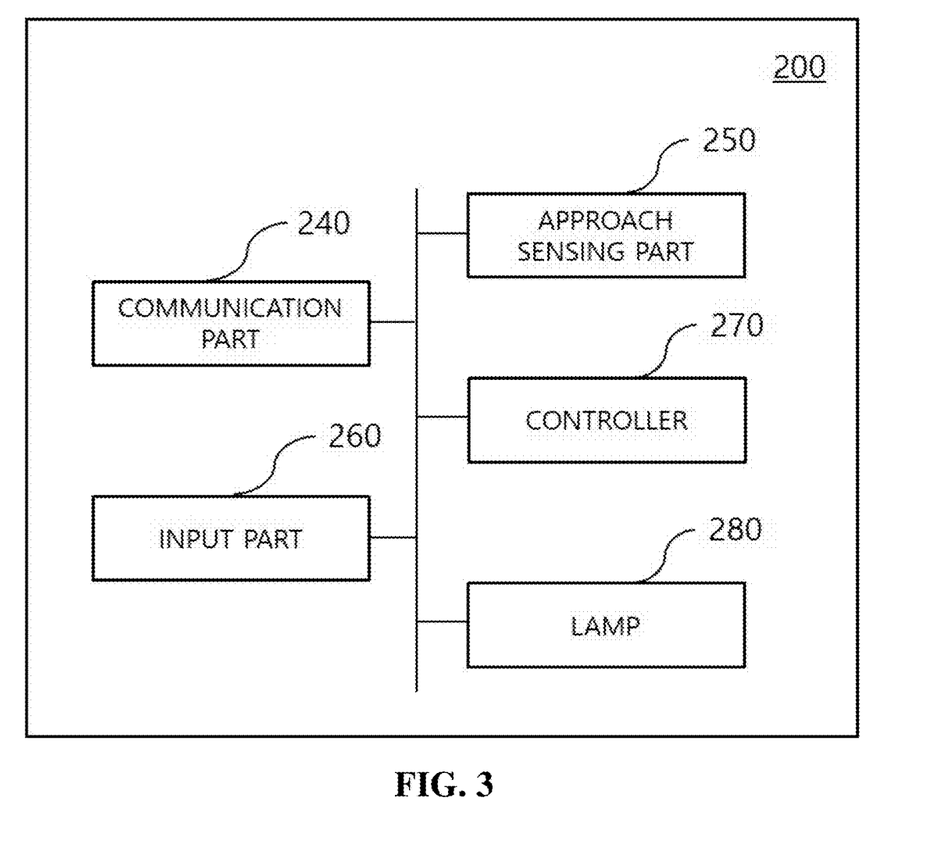
FIG. 3 is a schematic block diagram showing the multi-functional table configuration according to the embodiment of the present disclosure.

FIG. 2 is a perspective view showing a structure of the multi-functional table according to the embodiment of the present disclosure, and FIG. 3 is a block diagram showing the multi-functional table according to the embodiment of the present disclosure.

Referring to FIGS. 2 and 3, the multi-functional table 200 includes at least one of a first plate 210, a second plate 220, at least one support part 230, a communication part 240, an approach sensing part 250, an input part 260, a controller part 270, and a lamp 280.

The at least one plate includes the first plate 210 and the second plate 220. The first plate 210 and the second plate 220 can be arranged not to overlap one another. Each of the first plate 210 and the second plate 220 can be arranged in parallel to the surface of ground, or can be arranged to have a predetermined angle to the ground.

The at least one support part 230 can have a pair of plates which are symmetrically arranged to each other. The at least one support part 230 can support the at least one plate such as the first plate 210 and the second plate 220. The at least one support part 230 can adjust each height of the at least one plate including the first plate 210 and the second plate 220 either at the same time or in an order according to the control of the controller part 270. Each of the heights of the first plate 210 and the second plate 220 is adjusted by the at least one support part 230 using a conventional method such as electric or mechanical methods.

The communication part 240 receives the user information from the user terminal 100. As the user information is described along with FIG. 1 above, the user information can include at least any one of the holding time information, the user identification information, the user physical information, or the user's operation mode information (i.e. a sitting mode or a standing mode). Further, the communication part 240 transmits alarming information to the user terminal 100, where the alarming information can include an expiration of the sitting time in the sitting mode and a change of the user's posture in the standing mode.

The approach sensing part 250 senses whether the user terminal 100 approaches the table 200. For example, if the user terminal 100 approaches within a predetermined radius from the table 200, the approach sensing part 250 produces approach information and transmits the approach information to the controller part 270. If the controller part 270 receives the approach information, the lamp 280 is turned on by the control of the controller part 270.

On the other hand, the reception of the user information to the communication part 240 may occur when the approach of the approach sensing part 250 is sensed. That is, if the controller part 270 receives the approach information from the approach sensing part 250, it requests the user information to the user terminal 100 through the communication part 240 and receives the user information from the user terminal 100.

The input part 260 receives the selection information of the sitting mode or standing mode from the user and manual adjustment information for the respective heights of the first plate 210 and the second plate 220. For example, the input part 260 includes at least one switch, but is not limited thereto.

The controller part 270 controls the operations of the at least one support part 230 in response to the user information received from the communication part 240 and the selection information for the operation mode and the manual adjustment information received from the input part 260. The controller part 270 controls the at least one support part 230 in accordance with at least any one of the user's operation mode information (i.e. the sitting mode or standing mode), the holding time information, the user identification information, and the user physical information and adjusts each height of the first plate 210 and the second plate 220 independently.

For example, if the operation mode of the user information is in the sitting mode, the controller part 270 controls the at least one support part 230 so that each of the first plate 210 and the second plate 220 has a predetermined height in response to the sitting mode. Further, for example, if the user identification information and/or the user physical information are further included in the user information, the controller part 270 additionally controls the at least one support part 230 so that each of the first plate 210 and the second plate 220 has a predetermined height, for the user corresponding to the user identification information, or a predetermined height in response to the user physical information.

Moreover, if the holding time for the sitting mode has elapsed in the sitting mode, the controller part 270 is configured to control the at least one support part 230 so that each of the heights of the first plate 210 and the second plate 220 is set from a height for the sitting mode to a height for the standing mode. Otherwise, the controller part 270 controls the at least one support part 230 so that each of the heights of the first plate 210 and the second plate 220 is adjusted to heights for the standing mode according to the selection information which is a command to convert to the standing mode and inputted by the user. Accordingly, the controller part 270 guides the user to change his or her posture not to use the multi-functional table 200 in the sitting position more than a predetermined period of time, thereby improving the user's spinal health through the change of the user's posture.

Further, if the holding time for the standing mode has elapsed in the standing mode, the controller part 270 controls the at least one support part 230 so that each of the heights of the first plate 210 and the second plate 220 set in response to the standing mode can be adjusted to heights set in response to the sitting mode, and otherwise, the controller part 270 controls the at least one support part 230 so that each of the heights of the first plate 210 and the second plate 220 can be adjusted the heights in response to the sitting mode according to the selection information, which is input by the user through a converting command to the sitting mode.

Furthermore, the controller part 270 controls the at least one support part 230 so that the first plate 210 and the second plate 220 have predetermined heights in accordance with the user identification information and/or the user physical information included in the user information. At this time, the heights of the first plate 210 and the second plate 220 according to the user identification information and/or the user's physical information are set in response to the respective sitting and standing modes. For example, the controller part 270 controls the at least one support part 230 so that in the sitting mode the first plate 210 and the second plate 220 have predetermined heights (for example, a user, Hong Kil-Dong has a height of the first plate 210 of 70 cm and a height of the second plate 220 of 100 cm) set for the user corresponding to the user identification information.

If the holding time for the sitting mode and/or the standing mode set by the user has elapsed, further, the controller part 270 produces alarming information and transmits the alarming information to the user terminal 100 and/or the lamp 280.

The lamp 280 can be disposed on at least one of the first plate 210 and the second plate 220 and be turned on/off under the control of the controller part 270. For example, if the approach of the user terminal 100 is sensed by the approach sensing part 250, the lamp 280 is turned on by the control of the controller part 270. If the holding time for the sitting mode and/or the standing mode set by the user has elapsed, further, the lamp 280 receives the alarming information from the controller part 270 and is turned on/off or changes the color of the irradiating light thereof.

Now, the details of the operations of the multi-functional table 200 according to respective operating modes will be described.

Figure 4:
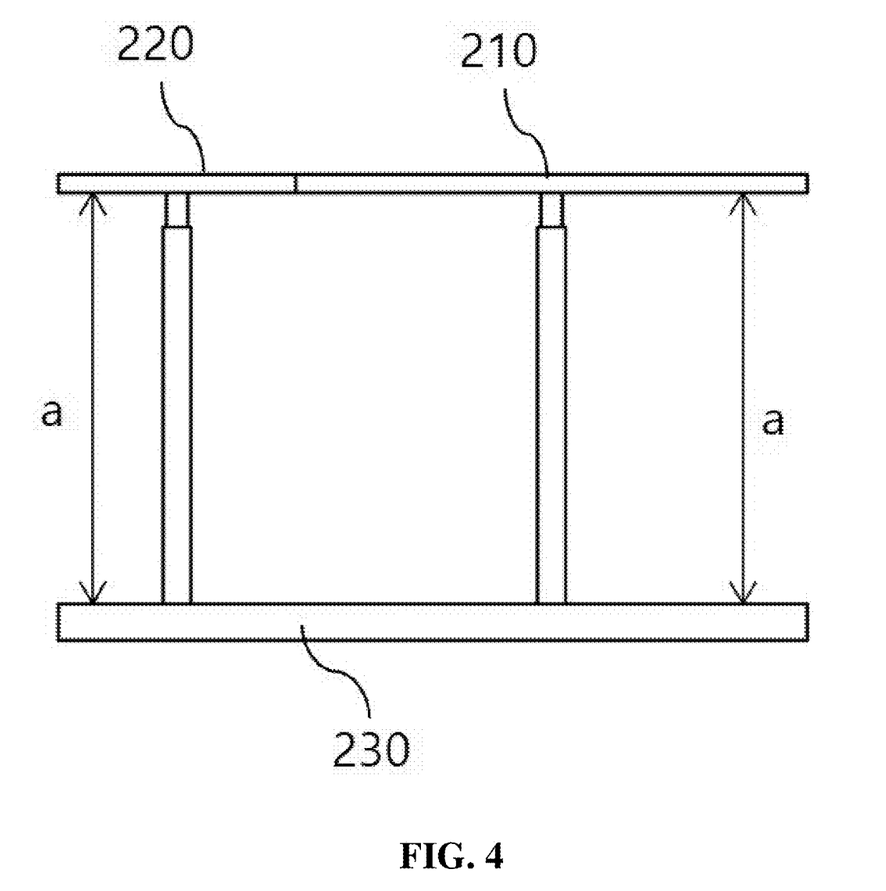
FIG. 4 is a side view showing an operation in a standby mode of the multi-functional table according to the embodiment of the present disclosure.
Figure 5:
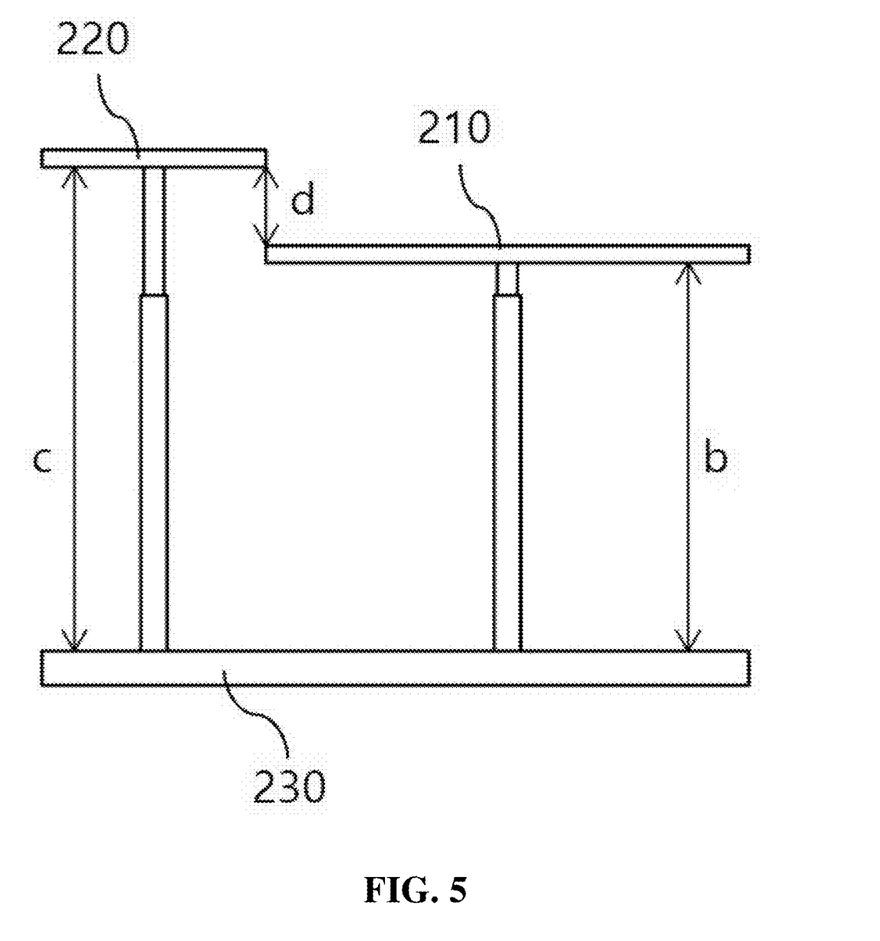
FIG. 5 is a side view showing an operation in a sitting mode of the multi-functional table according to the embodiment of the present disclosure.
Figure 6:
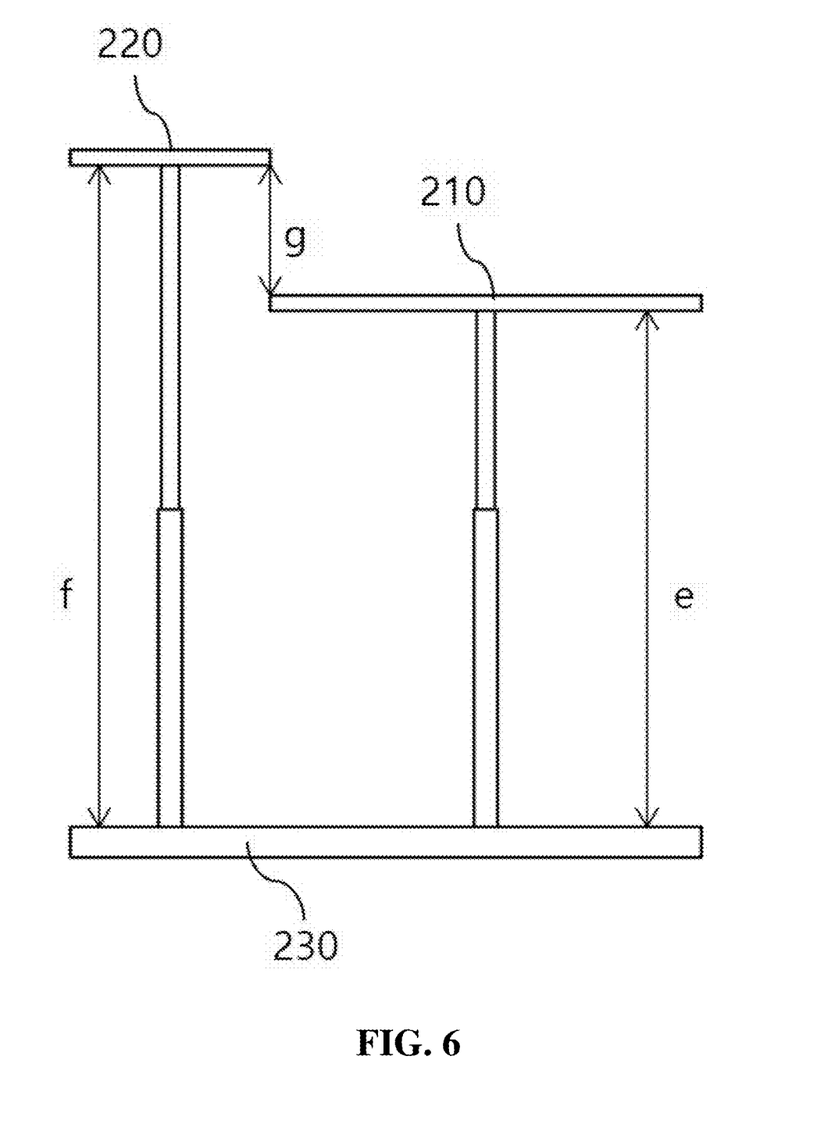
FIG. 6 is a side view showing an operation in a standing mode of the multi-functional table according to the embodiment of the present disclosure.

FIG. 4 is a side view showing an operation in a standby mode of the multi-functional table according to the embodiment of the present disclosure. FIG. 5 is a side view showing an operation in a sitting mode of the multi-functional table according to the embodiment of the present disclosure. FIG. 6 is a side view showing an operation in a standing mode of the multi-functional table according to the embodiment of the present disclosure.

Referring to FIG. 4, for example, if the sitting mode or standing mode selection information is not received from the user terminal 100 or the input part 260, the multi-functional table 200 remains in a standby mode. In the standby mode, the first plate 210 and the second plate 220 can be arranged to have the same height 'a'. In this case, the user can use the first plate 210 and the second plate 220 as a single combined flat plate.

Referring to FIG. 5, the controller part 270 of the multi-functional table 200 adjusts the multi-functional table 200 to a sitting mode in response to the user information or the selection information for the operation modes. In more detail, the controller part 270 controls the at least one support part 230 so that the height of the first plate 210 is 'b' and the height of the second plate 220 is 'c'. The heights 'b' and 'c' are differently adjusted in accordance with the user identification information and the user physical information.

Referring to FIG. 5, as one of the exemplaries, the height 'b' of the first plate 210 is lower than the height 'c' of the second plate 220. The example of the heights is of course not limited thereto. The height 'b' of the first plate 210 may be higher than or equal to the height 'c' of the second plate 220. In a case that a keyboard for a personal computer is disposed on the first plate 210 and a monitor for the personal computer on the second plate 220, the height 'b' of the first plate 210 can be lower than the height 'c' of the second plate 220 in consideration of a user's posture (for example, a turtle neck) and his or her eyesight protection.

Referring to FIG. 6, the controller part 270 of the multi-functional table 200 adjusts the multi-functional table 200 to a standing mode in response to the user information or the selection information for the operation modes. In more detail, the controller part 270 controls the at least one support part 230 so that the height of the first plate 210 has 'e' and the height of the second plate 220 is 'f'. The difference 'g' between the heights of the first plate 210 and the second plate 220 in the standing mode is larger than the difference 'd' between the heights of the first plate 210 and the second plate 220 in the sitting mode. This is set to provide a user's comfortable position and conveniences in use.

The height 'e' of the first plate 210 and the height 'f' of the second plate 220 are differently adjusted in accordance with the user identification information and the user physical information. As shown in FIG. 6, the height 'e' of the first plate 210 is lower than the height 'f' of the second plate 220 in the standing mode, but the example is not limited thereto. For instance, the height 'e' of the first plate 210 may be higher than or equal to the height 'f' of the second plate 220.

On the other hand, a change between the sitting mode and the standing mode can be repeatedly carried out for plural times based on a predetermined period of holding time. For example, if the predetermined period of holding time in the sitting mode or standing mode has elapsed, the conversion from one mode into the other mode can be automatically carried out to adjust the heights of the first plate 210 and the second plate 220. Further, for another example, if the holding time has elapsed, the alarming information indicating the elapsed holding time is provided to the user through, for instance, the user terminal 100 and/or the lamp 280, and the conversion from one mode into the other mode is carried out through the mode conversion command made by the user to adjust the heights of the first plate 210 and the second plate 220.

Figure 7A:
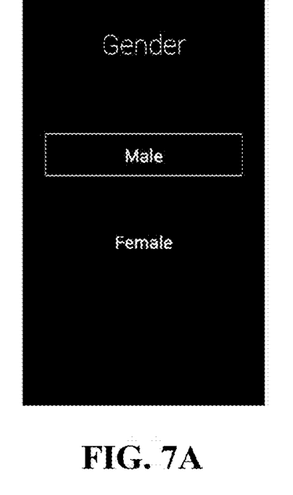
FIGS. 7A to 7C show exemplary screens of a user terminal in the table control system according to the embodiment of the present disclosure.
Figure 7B:
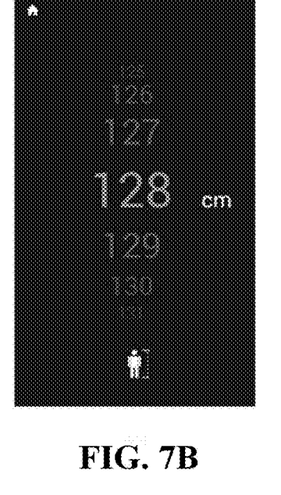
Figure 7C:
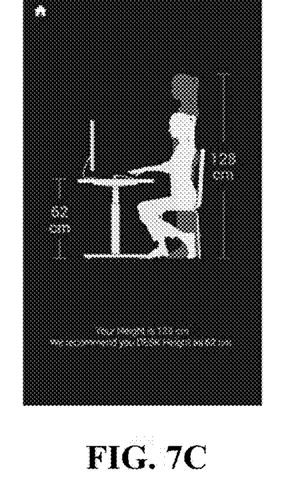

FIGS. 7A to 7C show exemplary screens of the user terminal 100 in the table control system according to the embodiment of the present disclosure.

Referring to FIGS. 7A to 7C, the user terminal 100 receives the user physical information from the user through a predetermined application. The physical information is contained in the user information, together with the user identification information, and is transmitted to the multi-functional table 200. The multi-functional table 200 adjusts the heights of the first plate 210 and the second plate 220 in response to the physical information.

According to the embodiment of the present disclosure, further, the user terminal 100 can detect and display the heights and/or holding time of the first plate 210 and/or the second plate 220 which are recommended for the respective operation modes in response to the physical information input thereto. In response to the physical information of the user such as the user's sex, height, and weight, the user terminal 100 can detect the heights and/or holding time of the first plate 210 and/or the second plate 220; recommend values for the respective operation modes; and display the recommended values on the screen. With the recommended values through the input to the user terminal 100, the user can set the heights and/or holding time of the first plate 210 and/or the second plate 220 with respect to the operation modes.

Figure 8A:
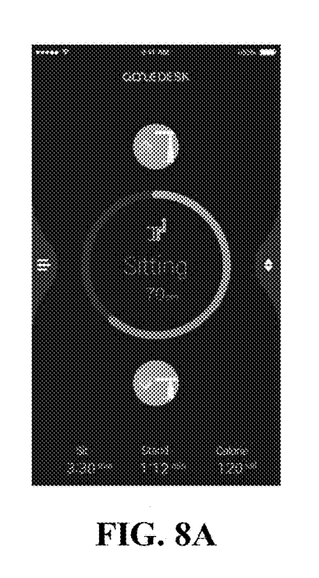
FIGS. 8A to 8C show other exemplary screens of a user terminal in the table control system according to the embodiment of the present disclosure.
Figure 8B:
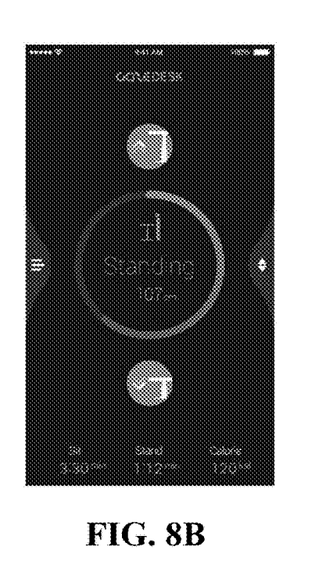
Figure 8C:
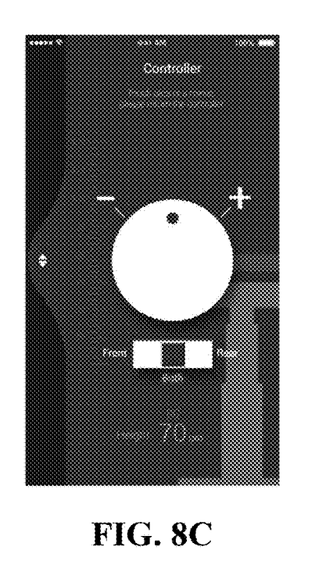

FIGS. 8A to 8C show other exemplary screens of the user terminal in the table control system according to the embodiment of the present disclosure.

Referring to FIGS. 8A to 8C, the user terminal 100 receives the current state information of the multi-functional table 200 and displays the current state information through a predetermined application. Further, the user terminal 100 receives manual control input information from the user so as to manually control the operation of the multi-functional table 200.

In more detail, the user terminal 100 receives the current state information of the multi-functional table 200 such as the operation mode currently carried out, the current heights of the first plate 210 and/or the second plate 220, and the elapsed time in the current operation mode, and displays the current state information on the screen.

Further, the user terminal 100 provides a user interface for the manual setting and changing of the heights of the first plate 210 and/or the second plate 220 according to the conversion of the operation mode or the operation modes, receives predetermined input information from the user, and transmits the received input information to the multi-functional table 200. The user interface desirably has the structure and shape corresponding to the input part 260 of the multi-functional table 200.

Figure 9A:
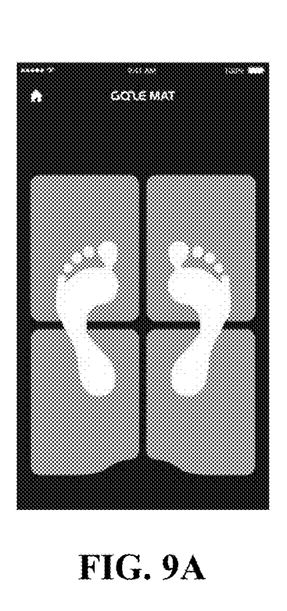
FIGS. 9A to 9C show other exemplary screens of a user terminal in the table control system according to the embodiment of the present disclosure.
Figure 9B:
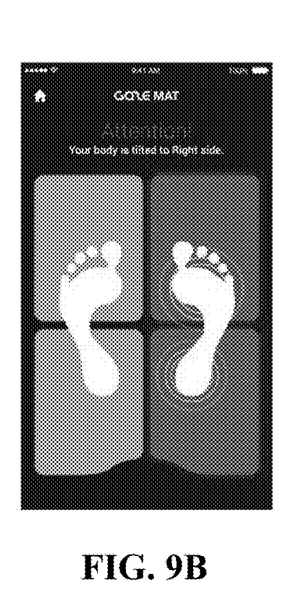
Figure 9C:
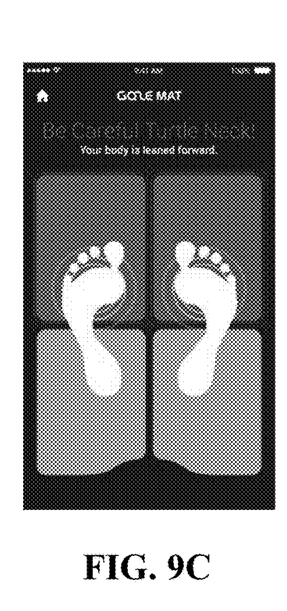

FIGS. 9A to 9C show other exemplary screens of the user terminal in the table control system according to the embodiment of the present disclosure.

Referring to FIGS. 9A to 9C, the user terminal 100 provides the user's posture information in the standing mode through a predetermined application. The posture sensing part 400 senses the user's posture in the standing mode through his or her both feet's pressures and transmits the user's posture information directly or indirectly to the user terminal 100. Otherwise, the user's posture information can be transmitted to the user terminal 100 through the multi-functional table 200. The user terminal 100 displays the user's posture information on the screen through a predetermined interface.

In particular, the user terminal 100 can receive alarming information indicating the user's posture is abnormal from the posture sensing part 400 and displays the alarming information thereon. For example, as shown in FIGS. 9A to 9C, the user terminal 100 provides the interface corresponding to the posture sensing part 400 and the user's feet on the screen, and through the comparison of an abnormal state wherein an excessive load is applied to one of both feet or portion of the feet with a normal state, the user terminal 100 displays the abnormal state in a predetermined manner. Accordingly, the user's proper posture correction can be guided through the table control system 1000.

As described above, the present disclosure can automatically adjust the height of the multi-functional table 200 to an appropriate customized height according to the physical conditions of the user, thereby improving the user's conveniences in use.

In addition, the present disclosure can allow the user to use the multi-functional table 200 in a sitting or standing position through the selection of the sitting mode or the standing mode, thereby improving the user's spinal health through his or her posture correction.

Further, the present disclosure can provide alarming information to the user if a predetermined period of time has elapsed in the sitting/standing modes, so that the conversion to another standing mode is guided, thereby improving the user's spinal health through his or her posture correction.

On the other hand, the embodiments of the present disclosure are carried out by hardware, middleware, microcode, software and/or their combination. For example, the embodiments of the present disclosure are carried out by one or more application specific integrated circuits ASICs, digital signal processors DSPs, digital signal processing devices DSPDs, programmable logic devices PLDs, field programmable gate arrays FPGAs, processors, controllers, microcontrollers, microprocessors, different electronic units capable of conducting the functions suggested herein, or their combination.

Further, the embodiments of the present disclosure are recorded or encoded on a computer-readable medium in which commands are contained. The commands recorded or encoded on the computer-readable medium are carried out through a programmable processor or another processor. The computer-readable medium includes a computer storage medium and a communication medium having an arbitrary medium capable of easily transferring computer program from one place to another place. The storage medium may be an arbitrary available medium accessible by a computer. For example, the computer-readable medium includes RAM, ROM, EEPROM, CD-ROM, other optical disc storage media, magnetic disc storage media, other magnetic storage devices, or arbitrary storage media capable of returning or storing desired program codes to the form of commands or data structures accessible by a computer.

The hardware, software, firmware and so on are carried out in the same device or individual devices so as to support various operations and functions suggested in the present disclosure. Additionally, the 'parts', 'units', 'module', and 'components', as used herein, are interoperable logic devices capable of being individually carried out. The description on the different features between the modules or units is intended to emphasize their different functions, and it does not mean the modules or units should be operated by individual hardware or software components. Contrarily, the functions related to one or more modules or units are carried out by individual hardware or software components, or their operations are shown in the drawing in a specific common order. However, it is not necessary that the operations are carried out in the specific order as shown in the drawing or in a sequential order and all of the operations as shown should be carried out, so as to achieve desired results. In an arbitrary environment, multitasking and parallel processing may be advantageous. Furthermore, the classification of the various components in the embodiment of the present disclosure are not necessarily applied to all embodiments of the present disclosure, and it should be understood that the components are integrated to a single software product or packaged to a plurality of software products.

The specific exemplary embodiments of the present disclosure have been illustrated in the drawings and described in detail in the detailed description. In the description, the terms, such as ones defined in common dictionaries, should be interpreted as having the same meanings as terms in the context of pertinent technology, and should not be interpreted as having ideal or excessively formal meanings unless clearly defined in the specification. It is to be appreciated that those skilled in the art can change or modify the embodiments without departing from the scope and spirit of the present disclosure. It is therefore intended that the scope of the disclosure be limited not by this detailed description, but rather by the claims appended hereto.

What is claimed is:

1. A multi-functional table comprising:
at least two plates;
at least two support parts, each of the at least two support parts connected to each of the at least two plates, respectively and adjusting a height of each of the at least two plates, independently;
a communication part receiving user information from a user terminal; and
a controller part controlling the height of each of the at least two plates in response to the user information, which is received from the communication part, wherein the at least two plates are configured to be separated from one another and to have the same or different height as the at least two support parts change the height of each of the at least two plates.

2. The multi-functional table of claim 1, wherein the at least two plates comprise a first plate and a second plate, and wherein the first plate and the second plate are arranged not to overlap one another.

3. The multi-functional table of claim 1, wherein the user information comprises operation mode information having at least one of a sitting mode and a standing mode.

4. The multi-functional table of claim 3, wherein the controller part has a configuration to control the at least two support parts to adjust the height of each of the at least two plates, respectively according to the operation mode.

5. The multi-functional table of claim 4, wherein the user information further comprises holding time information for each of at least one of the sitting mode and the standing mode, and
wherein if the holding time of the sitting mode has elapsed during the sitting mode, the controller part controls the at least two support parts to adjust the height of each of the at least two plates as set in the standing mode, and if the holding time of the standing mode has elapsed during the standing mode, the controller part controls the at least two support parts to adjust the height of each of the at least two plates as set in the sitting mode.

6. The multi-functional table of claim 5, wherein the controller part transmits alarming information to the user terminal if the holding time of at least one of the sitting mode and the standing mode has elapsed.

7. The multi-functional table of claim 1, wherein the user information comprises at least one of user identification information and user physical information, wherein the user identification information includes at least one of user identification and a user name, and wherein the user physical information includes at least one of a user's sex, age, height, weight, and sitting height.

8. The multi-functional table of claim 7, wherein the controller part controls the at least two support parts to adjust the height of each of the at least two plates in response to at least one of the user identification information and the user physical information.

9. The multi-functional table of claim 1, further comprising:
an approach sensing part sensing an approach of the user terminal to produce approach information; and
a lamp disposed on one of the at least two plates, wherein if the controller part receives the approach information from the approach sensing part, the lamp is turned on by the control of the controller part.

10. The multi-functional table according to claim 1, further comprising an input part receiving selection information for the sitting mode or the standing mode from the user.

11. The multi-functional table of claim 10, wherein when no selection information is received and the multi-functional table is in a standby mode, each of the at least two plates has a same height.

12. The multi-functional table of claim 1, wherein the controller part has a configuration to repeatedly change the modes between the sitting mode and the standing mode for a predetermined times.

13. The multi-functional table of claim 1, wherein the controller part has a configuration to change the modes between the sitting mode and the standing mode based on holding time of at least one of the sitting mode and the standing mode.

14. A table control system comprising:
a user terminal producing user information; and
a multi-functional table comprising:
at least two plates,
at least two support parts, each of the at least two support parts connected to each of the at least two plates, respectively and adjusting a height of each of the at least two plates, independently,
a communication part receiving user information from a user terminal, and
a controller part controlling the height of each of the at least two plates in response to the user information which is received from the communication part,
wherein the at least two plates are configured to be separated from one another and to have the same or different height as the at least two support parts change the height of each of the at least two plates.

15. The table control system of claim 14, wherein the user information comprises operation mode information having at least one of a sitting mode and a standing mode.

16. The table control system of claim 15, further comprising a posture sensing part sensing a user posture through pressures and positions of the user's feet,
wherein if the user's posture is sensed as deviated a predetermined posture in the standing mode, the posture sensing part transmits alarming information to at least one of the user terminal and a lamp disposed on the at least one plate.

17. The table control system of claim 15, further comprising a seating part sensing a sitting time of the user and transmitting the sitting time to the controller part,
wherein if the sitting time exceeds a predetermined period of time in the sitting mode, the controller transmits alarming information to at least one of the user terminal and a lamp disposed on the at least one plate.

18. The table control system of claim 14, wherein the user terminal provides the interface corresponding to the posture sensing part and the user's feet on the screen, and through the comparison of an abnormal state wherein an excessive load is applied to one of both feet or portion of the feet with a normal state, the user terminal displays the abnormal state in a predetermined manner.

19. The multi-functional table of claim 1 further comprising a posture sensing part senses a user posture through pressures and positions of the user's feet,
wherein if the user's posture is sensed as deviated a predetermined posture, the posture sensing part transmits alarming information to at least one of the user terminal and a lamp disposed on one of the at least two plates.

* * * * *